United States Patent [19]

Fisher

[11] Patent Number: 4,778,999
[45] Date of Patent: Oct. 18, 1988

[54] METHOD FOR DETECTING THE PRESENCE OF ADHESIVE IN A CONTAINER AND ASSOCIATED APPARATUS

[75] Inventor: Edward J. Fisher, Library, Pa.

[73] Assignee: American Glass Research, Inc., Butler, Pa.

[21] Appl. No.: 139,728

[22] Filed: Dec. 30, 1987

[51] Int. Cl.$^4$ ............................................ G01N 21/64
[52] U.S. Cl. ............................ 250/461.1; 250/459.1; 209/578
[58] Field of Search ............... 250/458.1, 459.1, 461.1, 250/372, 302; 209/578

[56] References Cited

U.S. PATENT DOCUMENTS

| | | | |
|---|---|---|---|
| 3,351,760 | 11/1967 | Brown | 250/302 |
| 3,617,744 | 11/1971 | Irish | 250/461.1 |
| 4,460,274 | 7/1984 | Schumann et al. | 356/318 |

FOREIGN PATENT DOCUMENTS 423019  4/1974  U.S.S.R. ............................ 250/458.1

Primary Examiner—Carolyn E. Fields
Attorney, Agent, or Firm—Arnold B. Silverman

[57] ABSTRACT

A method of inspecting a container for the presence of adhesive in desired locations includes providing an ultraviolet light source which impinges ultraviolet light on the locations where adhesive is desired and sensors which receive fluorescent light from the adhesives and thereby determine which locations have the desired adhesives. The sensors emit signals which may be employed to directly or indirectly cause rejection of any container not having adhesive at the desired locations. It is preferred to use long wavelength ultraviolet light on the order of about 325 nm to 375 nm. The apparatus provides a container supporting member, an ultaviolet light source in overlying relationship with the container and sensors which receive light fluorescing in the adhesives at the desired locations. It is preferred that the ultraviolet light source means be disposed between the container and the sensors and that the sensors have a plurality of independent individual or sets of sensor units which are adapted to receive fluorescent light from a single source.

18 Claims, 3 Drawing Sheets

METHOD FOR DETECTING THE PRESENCE OF ADHESIVE IN A CONTAINER AND ASSOCIATED APPARATUS

BACKGROUND OF THE INVENTION

1. Field Of The Invention

The present invention relates to a method and associated apparatus for automatically inspecting containers in order to confirm the presence of adhesive material at desired locations.

2. Description Of The Prior Art

It has been known to manufacture containers having a generally cup-like base portion which may be made of polyethylene having an annular base wall and an annular side wall extending upwardly and outwardly therefrom. By providing discrete locations with a suitable hot melt adhesive, a bottle composed of a suitable material such as polyethylene terephthalate may be secured to the base portion. In this type of assembly the base provides an economically feasible inexpensive base member and the bottle or other container may be made of an inexpensive relatively thin material depending upon whether the contents will be pressurized or not. The lower portion of the container is generally hemispherical as this is an efficient and economical way to manufacture a container for pressurized contents. It is apparent that an important aspect of this type of a container assembly is that the desired amount of adhesive be provided at the desired number of locations in order to create an effective bond between the base and the bottle.

One of the problems in connection with this type of container is that occasionally adhesive spray nozzles which apply adhesive to the locations on the base will clog and result in the base not receiving the desired adhesive at the desired spots. For example, if it is determined that three adhesive spots are required in order to securely bond the base to the overlying container, frequently a manufacturer will employ a fourth adhesive spot in order to enhance the likelihood that at least three adhesive spots will be present. While this does, in fact, minimize the risk of there not being the desired minimum of three adhesive spots, for example, it is wasteful of adhesive material.

It has also been known in a different environment that where a coating is provided with multiple layers of substances having different luminescent properties, telescopic examination of the materials may be employed. See U.S. Pat. No. 4,460,274.

There remains a very real and substantial need for inspection apparatus which can effectively and accurately determine whether adhesive is located at the desired minimum number of locations required in order to secure a container base to an overlying container.

SUMMARY OF THE INVENTION

The present invention has solved the above-described problems by providing a source of ultraviolet light which causes ultraviolet light to be directed onto the locations where it is desired to have hot melt adhesive. If adhesive is present the ultraviolet light will cause the adhesive to fluoresce in the visible spectral region. Sensor means are provided for receiving the fluorescent light from the locations when adhesive is present. The sensor means emit responsive signals confirming that adhesive is present at a particular location. The information may be visually displayed in order to permit an operator to energize a reject mechanism which will physically segregate a base which does not have adequate adhesive at a minimum number of locations or automatic means may be provided to cause the reject mechanism to reject a particular container base.

It is an object of the present invention to provide a method and apparatus for detecting whether desired adhesive is present at a plurality of locations on a container member and emitting indications of the presence of such adhesive at one or more locations.

It is a further object of the invention to employ the method and apparatus to facilitate detection of one or more adhesive supply jets being non-functional.

It is a further object of the invention to facilitate savings in the cost of adhesive employed per container while maintaining high efficiency of bonding of a container to a container base.

It is a further object of the invention to employ such a system wherein light sensors receive light which fluoresces in adhesive while resisting interference from stray light sources.

These and other objects of the invention will be more fully understood from the following description of the invention on reference to the illustrations appended hereto.

DESCRIPTION OF THE PREFERRED EMBODIMENT

As used herein, the expression "container" unless a contrary indication is expressly provided at particular locations, shall mean either a component of a container having locations at which it is desired to provide adhesive or a complete container assembly having such a component.

Figure 1:
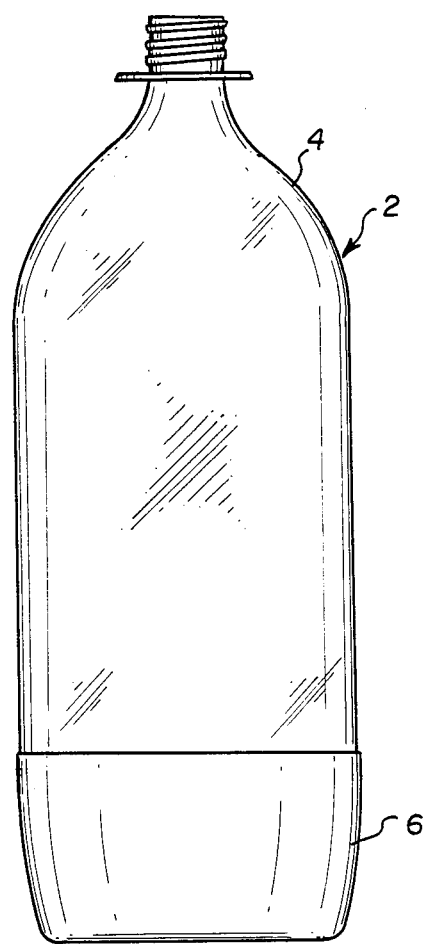
FIG. 1 is an elevational view of a container consisting of a base member which is adhesively secured to an overlying container.
Figure 2:
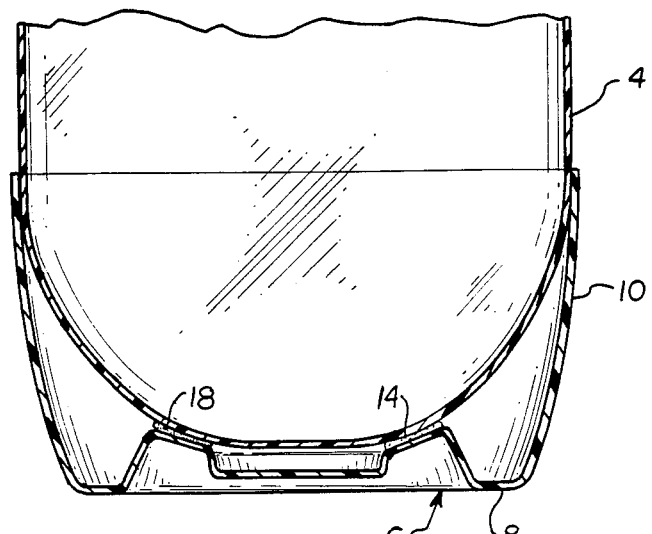
FIG. 2 is a partially schematic cross-sectional illustration of a portion of the base of the container of FIG. 1.

Referring to FIGS. 1 and 2, there is shown a container assembly 2 consisting of an upper bottle-like portion 4 and a generally cup-like base portion 6. The base portion 6 has a base wall 8 which may be annular in shape and a generally upwardly and outwardly projecting annular side wall 10. In creating the container assembly, adhesive is positioned at several spaced locations around the base 6 and the bottle 4 is urged into intimate contact therewith for a period long enough to cause the adhesive to set and establish an effective bond between the two components.

While it is not critical to the invention what the materials the base 6 or bottle 4 are made of, it will generally be convenient to employ a synthetic resinous base 6 and a bottle 4 composed of a synthetic resin or other suitable material. A frequently employed base 6 for such assemblies is composed of polyethylene and a suitable overlying bottle 4 may be made of polyethylene terephthalate. The adhesive employed is generally a hot melt adhesive such as one composed of polyamide, which is applied to the cup-like base member 6 at elevated temperature at the desired locations by conventional adhesive distributing nozzles.

Figure 3:
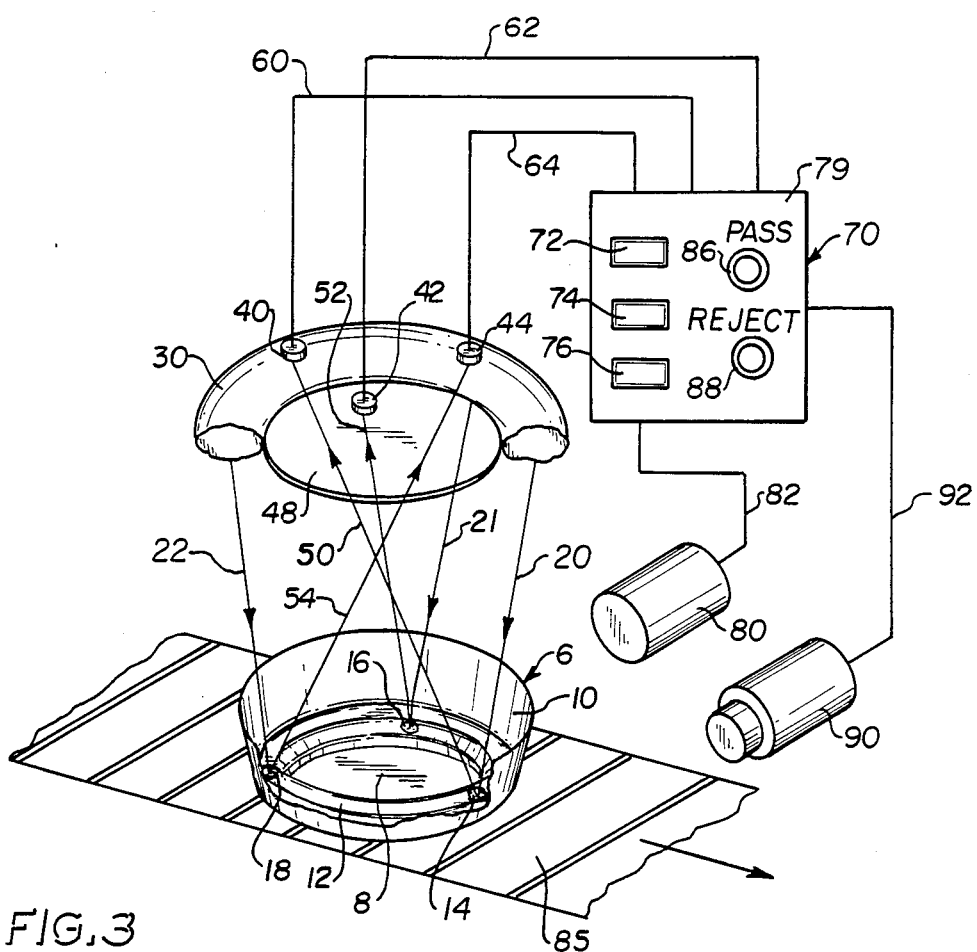
FIG. 3 is a schematic illustration of the apparatus employed in the present invention.
Figure 4:
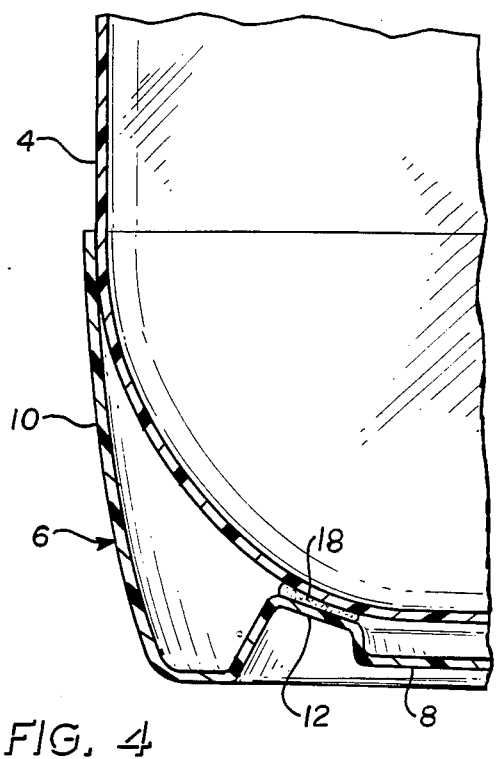
FIG. 4 is a partial cross-sectional illustration showing a portion of a container.

Referring to FIGS. 3 and 4, there is shown a container base 6, having a bottom wall 8, a generally upwardly and outwardly extending annular ledge 12 which conforms to the generally hemispherical shape of the lower portion of container body 4. In the form shown, the base has an annular ledge 12 to receive drops of adhesive from adhesive dispensers (not shown). In the form shown, adhesive is present at each of three relatively spaced locations 14, 16, and 18.

Annular light source means 30 provides ultraviolet light, preferably of long wave e.g. on the order of wavelengths of about 325 nm to 375 nm which is directed downwardly onto the locations 14, 16, 18 as indicated by the outer arrows 20, 21, 22. Ultraviolet light of this type strikes the adhesive at locations 14, 16, 18 and the adhesive fluoresces. The fluorescent light is directed upwardly in the directions indicated by the upwardly pointing arrows 50, 52, 54 so as to impinge upon sensor means 40, 42, 44, respectively. The sensors may be of any desired form of photosensor which is adapted to receive light and convert it into responsive related output electrical signals. Among the types of photosensors preferred for this use are silicon photodiodes and silicon phototransistors. It will be appreciated, in the forms shown, a separate photosensor is provided for each adhesive location. For example, location 14 is connected by light beam 50 to sensor 40. Similarly, location 16 is connected by light beam 52 to sensor 42, and location 18 is connected by light beam 54 to sensor 44. It will be appreciated that lens 48 which is preferably a positive lens of about 40-60 mm focal length serves to facilitate focusing the fluorescent light emerging from the locations which have adhesive present onto the sensors 40, 42, 44. In the event that adhesive is not present at a given location or is not present in a desired minimum quantity, the sensor will not emit a responsive signal. In the event that adhesive is present in the desired amount, each sensor 40, 42, 44, which receives a light beam of desired intensity will emit responsive electrical signals over electrical lead 60, 62, 64, respectively, to the control and indicator means 70 which has a series of lights, 72, 74, 76, mounted on panel 79 with each light 72, 74, 76 corresponding to a particular sensor 40, 42, 44 so as to indicate which locations 14, 16, 18 have received adhesive in the desired amount. For example, if all three locations 14, 16, 18 receive the desired amount of adhesive all three lights 72, 74, 76 are illuminated. Assuming that sensor 42 is associated with light 74 and location 16 does not receive the desired quantity of adhesive, this light will not be illuminated. This provides an indication that the nozzle supplying adhesive to location 16 is not functioning or that some other aspect of adhesive supply to this location is not functioning.

Assuming that all three locations 14, 16, 18 are required to have a predetermined quantity of adhesive or the container will be considered defective, unless all three lights 72, 74, 76 are illuminated, the container will be rejected. In the alternative, if a minimum of two of the three containing adhesive at the locations is adequate, then illumination of two of the lights 72, 74, 76 would result in the container not being rejected, but only one light being illuminated would result in the container being rejected.

In the system shown in FIG. 3 the container base 6 is moved in the direction indicated by the arrow on the container support member 85 which in the form shown is a conveyor. In the event that the container base does not have the required amount of adhesive at locations 14, 16, 18, the control and indicator means 70 will actuate a reject mechanism 90. The reject mechanism 90 may be a conventional plunger type device adapted to extend toward the conveyor 85 and physically move the rejected base 6 off the conveyor. Pass lamp 86 and fail or reject lamp 88 are helpful for troubleshooting and set-up purposes. These lamps 86, 88 indicate that a base cup has or has not, respectively, the desired amount of adhesive at the desired spots.

Also shown in FIG. 3 is a sensor means 80 to sense the presence of the container base 6 and signal its presence over lead 82 to control and indicator means 70. This sensor may use photoelectric, ultrasonic or such other technology as is well known to those skilled in the art.

Figure 5:
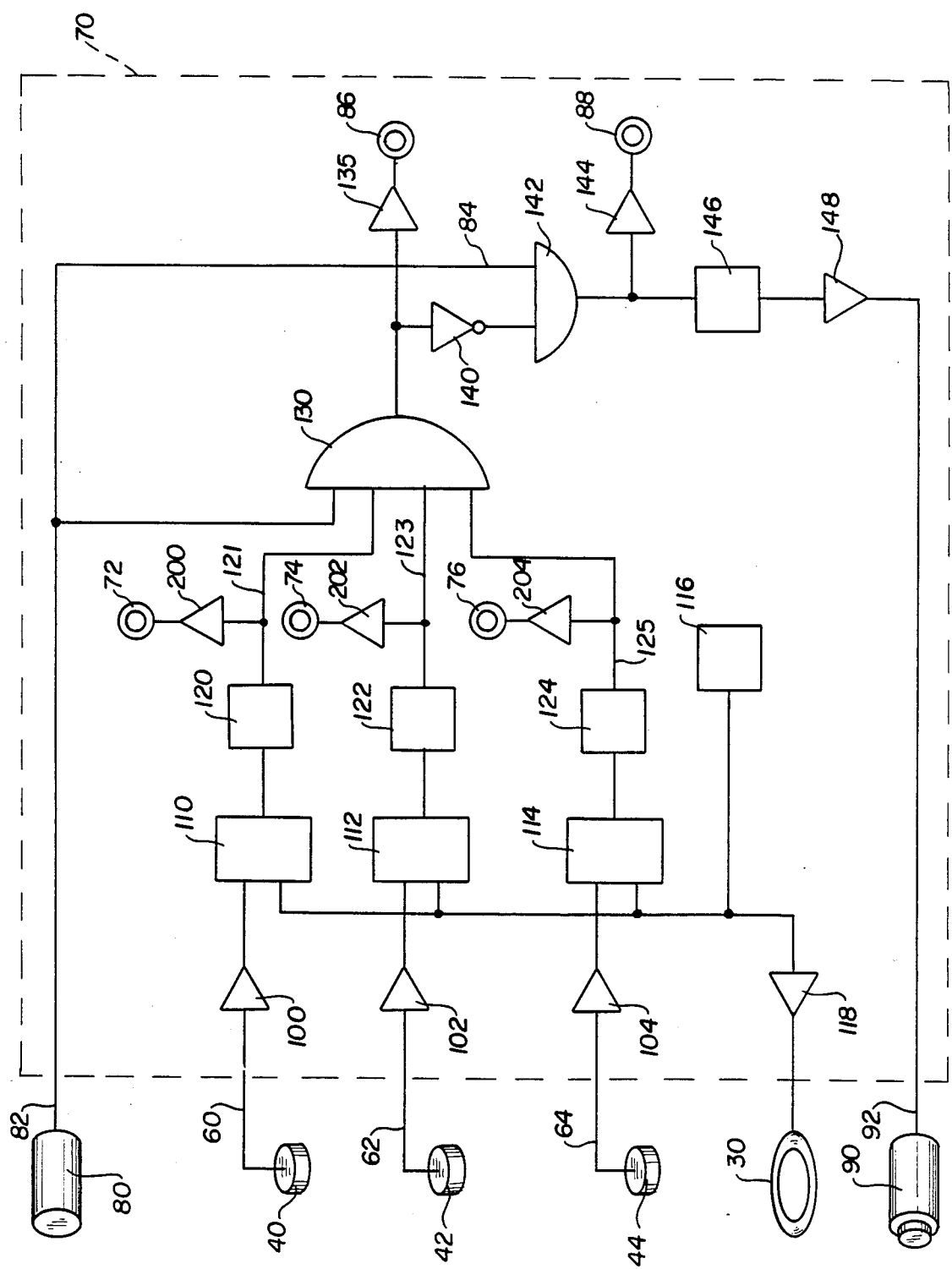
FIG. 5 is a schematic diagram showing electrical and control details of the invention.

Referring again to FIG. 5, the control and indicator means 70 accepts signals from the sensors 40, 42, 44 over leads 60, 62, 64, respectively. These signals are amplified by signal amplifiers 100, 102, 104, respectively. The amplified signals are carried to synchronous demodulators 110, 112, 114, respectively. The synchronous demodulators 110, 112, 114 are driven by an oscillator 116 running at twice the frequency of the AC mains. The oscillator 116 also drives a lamp driver 118 which in turn drives the ultraviolet lamp 30 which illuminates the container base 6 (in FIG. 3). Such synchronous demodulation, well known to those skilled in the art, resists interference from light from ordinary indoor lighting and also from sunlight. The demodulated signals are converted to logic levels (either TRUE or FALSE) by voltage comparators 120, 122, and 124. Thus, if sufficient light strikes, for example, sensor 40, a logic TRUE will be present on lead 121. Conversely, if no light strikes sensor 40, a logic FALSE will be present on lead 121. In like manner, the same function occurs in sensors 42 and 44 and "leads" 123 and 125. Logic AND gate 130 accepts the outputs from each of the voltage comparators 120, 122, 124 and from sensor 80 which, as described hereinbefore, senses the presence of a container base below the sensors 40, 42, 44. If a container is present a logic TRUE will be present on lead 82. Thus, the output of AND gate 130 will be TRUE if all signals from all sensors 40, 42, 44 are of sufficient magnitude, indicating the presence of a sufficient amount of adhesive present at locations 14, 16, 18 (see FIG. 3) and a container base is present below the sensors 40, 42, 44. A lamp driver 235 drives lamp 86 on the front panel of the indicator and control means 70 to indicate a PASS condition. If the output of AND gate 130 is not TRUE, logic inverter 140 drives AND gate 142. The other input of AND gate 142 is lead 84 which comes from sensor 80 which is TRUE when a container base is below sensors 40, 42, 44. The output of AND gate 142 is TRUE when a container base is present and one or more sensors are not illuminated. This will be recognized as the reject condition. Hence AND gate 142 drives a lamp driver 144 which drives reject lamp 88. AND gate 142 also drives a reject delay 146 which in turn drives reject driver 148 and reject mechanism 90.

Lamps 72, 74, 76 are operatively associated with sensors 40, 42, 44, respectively, with lamp drivers 200, 202, 204, respectively interposed.

It will be appreciated that the present invention provides an effective method and associated apparatus for economically and efficiently inspecting container base portions which have several relatively spaced discrete locations for application of adhesive to make sure that the adhesive is present at the required number of locations. The system provides means for rejecting those containers which do not have the desired amount of adhesive and also provide means for indicating whether certain adhesive dispensing nozzles are malfunctioning.

Whereas particular embodiments of the invention have been described above for purposes of illustration, it will be appreciated by those skilled in the art that numerous variations of the details may be made without departing from the invention as described in the appended claims.

I claim:

1. A method of inspecting a container for the presence of an adhesive in desired locations, comprising
providing ultraviolet light source means for impinging ultraviolet light on said locations to cause adhesive disposed at said locations to fluoresce,
providing sensor means for receiving fluoresced light which fluoresces from said adhesive disposed at said locations and emitting signals responsive to receipt of said fluoresced light,
positioning a said container in a position to receive said ultraviolet light at said locations,
directing said ultraviolet light on said locations,
monitoring light fluorescing from said adhesive disposed at said locations by said sensor means, and
emitting signals from said means responsive to receipt of fluorescent light from said locations, wherein the emitted signals will provide information as to which locations had adhesive present.

2. The method of claim 1 including
providing said container as a cup-like base with said locations disposed in relative spaced relationship on the interior thereof, and
inspecting each said location by means of a separate portion of said sensor means.

3. The method of claim 2 including
employing at least three said locations on said container.

4. The method of claim 3 including
rejecting any said containers not having the desired number of locations provided with adhesive responsive to information provided by said sensor means.

5. The method of claim 4 including
positioning said sensor means on the same side of said container as said ultraviolet light source means.

6. The method of claim 5 including
positioning said sensor means with respect to said ultraviolet light source means such that said light fluorescing in said adhesive will pass through an opening in said ultraviolet light source means in reaching said sensor means.

7. The method of claim 6 including
employing ultraviolet light of a wavelength of about 325 nm to 375 nm.

8. The method of claim 7 including
employing said emitted signal information to provide a visual indication of which locations have said adehesive present.

9. The method of claim 8 including
transporting said container on conveyor means to and from said ultraviolet light source means,
providing reject means downstream of said ultraviolet light source means, and
activating said reject means to reject a container responsive to said emitted signal information indicating that adhesive is not present at a desired number of said locations.

10. The method of claim 8 including
employing said method on a container base composed of polyethylene.

11. Apparatus for inspecting a container for the presence of an adhesive in desired locations comprising
a container supporting member,
ultraviolet light source means in spaced overlying relationship with respect to said container supporting member,
sensor means for receiving light fluorescing from adhesive receiving locations on a said container disposed on said container supporting member if adhesive is present at said locations and emitting a responsive signal, and
indicator means for receiving the emitted signals and indicating which locations have the desired adhesive present, wherein ultraviolet light impinging on adhesive disposed at said locations will cause the adhesive to fluoresce, the fluorescent light being picked up by said sensor means which will emit a responsive signal containing this information.

12. The apparatus of claim 11 including
reject means for rejecting a container responsive to receipt of said emitted signals indicating that a desired number of locations do not have said adhesive present.

13. The apparatus of claim 12 including
said ultraviolet light source means being of annular shape.

14. The apparatus of claim 13 including
sensor means being disposed on the opposite side of said ultraviolet light source means from said container supporting member.

15. The apparatus of claim 14 including
visual display means for indicating responsive to said sensor means emitted signal which of said locations has adhesive present.

16. The appartus of claim 15 including
said container supporting member including conveyor means for transporting said container to and away from said ultraviolet light source means.

17. The apparatus of claim 13 including
said sensor means being positioned to receive light from said locations which light passes through the annulus of said ultraviolet light source means.

18. The apparatus of claim 17 including
lens means for focusing said fluorescent light from said adhesive locations toward said sensor means.

* * * * *

UNITED STATES PATENT AND TRADEMARK OFFICE
CERTIFICATE OF CORRECTION

PATENT NO. : 4,778,999
DATED : October 18, 1988
INVENTOR(S) : EDWARD J. FISHER

It is certified that error appears in the above-identified patent and that said Letters Patent is hereby corrected as shown below:

Title page:

In the Abstract, line 12, "ultaviolet" should be --ultraviolet--.

Column 4, line 52, "235" should be --135--.

Claim 8, column 6, line 4, "adehesive" should be --adhesive--.

Claim 16, column 6, line 51, "appartus" should be --apparatus--.

Signed and Sealed this

Twenty-first Day of March, 1989

*Attest:*

DONALD J. QUIGG

*Attesting Officer*      *Commissioner of Patents and Trademarks*